(12) United States Patent
Qureshi et al.

(10) Patent No.: US 11,673,845 B2
(45) Date of Patent: Jun. 13, 2023

(54) AROMATIZATION OF LIGHT HYDROCARBONS USING METAL-MODIFIED ZEOLITE CATALYSTS

(71) Applicants: Saudi Arabian Oil Company, Dhahran (SA); King Fahd University of Petroleum and Minerals, Dhahran (SA)

(72) Inventors: Ziyauddin S. Qureshi, Dhahran (SA); Yaming Jin, Dhahran (SA); Abdullah M. Aitani, Khobar (SA); Omer Refa Koseoglu, Dhahran (SA); Mohammad Naseem Akhtar, Dhahran (SA); Hassan Saeed Al-Awad Alasiri, Dhahran (SA)

(73) Assignees: Saudi Arabian Oil Company, Dhahran (SA); King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 17/010,969

(22) Filed: Sep. 3, 2020

(65) Prior Publication Data
US 2022/0064081 A1 Mar. 3, 2022

(51) Int. Cl.
*C07C 2/42* (2006.01)
*B01J 23/06* (2006.01)
(Continued)

(52) U.S. Cl.
CPC ............. *C07C 2/42* (2013.01); *B01J 23/10* (2013.01); *B01J 23/28* (2013.01); *B01J 23/60* (2013.01);
(Continued)

(58) Field of Classification Search
None
See application file for complete search history.

(56) References Cited

U.S. PATENT DOCUMENTS 3,756,942 A * 9/1973 Cattanach ............... B01J 29/40
208/137
3,953,366 A 4/1976 Morrison
(Continued)

FOREIGN PATENT DOCUMENTS

CN 1232071 A * 10/1999
CN 106552663 A * 4/2017

OTHER PUBLICATIONS

CN106552663A English Translation obtained from Espacenet (Year: 2021).*
(Continued)

*Primary Examiner* — Philip Y Louie
(74) *Attorney, Agent, or Firm* — Dinsmore & Shohl LLP

(57) ABSTRACT

Embodiments of the present disclosure are directed to processes for aromatizing hydrocarbons includes contacting the hydrocarbons with a catalyst including at least two different metal modifiers dispersed on surfaces of a hydrogen-form medium-pore zeolite support. Each of the at least two different metal modifiers comprises a metal selected from the group consisting of IUPAC Groups 3-12, and lanthanide metals, and the catalyst is substantially free of gallium. Contacting the hydrocarbons with the catalyst causes a least a portion of the hydrocarbons to undergo a chemical reaction to form aromatic hydrocarbons.

13 Claims, 4 Drawing Sheets

(51) Int. Cl.
  B01J 23/10    (2006.01)
  B01J 23/28    (2006.01)
  B01J 23/60    (2006.01)
  B01J 29/40    (2006.01)
  C10G 35/095   (2006.01)

(52) U.S. Cl.
  CPC .......... *B01J 29/405* (2013.01); *C10G 35/095* (2013.01); *C07C 2523/10* (2013.01); *C07C 2523/28* (2013.01); *C07C 2523/60* (2013.01); *C07C 2529/40* (2013.01)

(56) References Cited

U.S. PATENT DOCUMENTS

| | | | |
|---|---|---|---|
| 4,157,293 A * | 6/1979 | Plank | B01J 29/40 |
| | | | 208/135 |
| 4,190,519 A | 2/1980 | Miller et al. | |
| 4,330,396 A * | 5/1982 | Miller | B01J 29/90 |
| | | | 208/136 |
| 4,861,934 A | 8/1989 | Suzuki et al. | |
| 5,055,437 A | 10/1991 | Herbst et al. | |
| 5,073,673 A | 12/1991 | Hirabayashi et al. | |
| 5,276,232 A | 1/1994 | Inoue et al. | |
| 5,958,216 A * | 9/1999 | Glover | C10G 59/02 |
| | | | 208/64 |
| 6,177,002 B1 | 1/2001 | Glover | |
| 6,190,534 B1 | 2/2001 | Bogdan | |
| 7,285,696 B2 | 10/2007 | Schmidt et al. | |
| 7,589,041 B2 | 9/2009 | Ying et al. | |
| 10,427,142 B1 | 10/2019 | Al-Herz et al. | |
| 10,519,387 B2 | 12/2019 | Ravishankar et al. | |
| 10,596,558 B2 | 3/2020 | Arvind et al. | |
| 11,021,422 B1 | 6/2021 | Koseoglu | |
| 2004/0110630 A1 | 6/2004 | Schmidt et al. | |
| 2004/0236164 A1 | 11/2004 | Rangarajan et al. | |
| 2011/0132804 A1 | 6/2011 | Stevenson et al. | |
| 2012/0024776 A1 | 2/2012 | Garcia-Martinez | |
| 2012/0277503 A1 | 11/2012 | Wegerer et al. | |
| 2012/0283494 A1 | 11/2012 | Smith et al. | |
| 2013/0085311 A1 | 4/2013 | Youn et al. | |
| 2014/0316179 A1 | 10/2014 | Ghosh et al. | |
| 2016/0030931 A1 | 2/2016 | Kelkar et al. | |
| 2017/0088485 A1* | 3/2017 | Shekyar | C07C 2/76 |
| 2017/0114288 A1 | 4/2017 | Ravishankar et al. | |
| 2017/0144138 A1 | 5/2017 | Arvind et al. | |
| 2017/0305812 A1 | 10/2017 | Keusenkothen et al. | |
| 2018/0066197 A1 | 3/2018 | Koseoglu et al. | |
| 2018/0194636 A1 | 7/2018 | Cheng et al. | |
| 2018/0305273 A1 | 10/2018 | Patel et al. | |
| 2019/0224653 A1 | 7/2019 | Koseoglu et al. | |
| 2020/0407649 A1 | 12/2020 | Lapinski et al. | |
| 2022/0025276 A1 | 1/2022 | Koseoglu et al. | |

OTHER PUBLICATIONS

CN 1232071 A English Translation, pp. 1-7 (Year: 2022).*
Aitani et al., "Catalytic Upgrading of Light Naphtha to Gasoline Blending Components: A Mini Review", Energy & Fuels, vol. 33, pp. 3828-3843, 2019.
Bhan et al., "Propane Aromatization over HZSM-5 and Ga/HZSM-5 Catalysts", Catalysis Reviews, vol. 50, pp. 19-151, 2008.
Dicksson et al., "The Future of Petrochemicals: Growth Surrounded by Uncertainty", Deloitte, New York, 2019.
Hodala et al., "Aromatization of C5-rich Light Naphtha Feedstock over Tailored Zeolite Catalysts: Comparison and Model Compounds (n-C5-n-C7)", ChemPubSoc Europe, Chemistry Select, 1, pp. 2515-2521, 2016.
Meriaudeau et al., "Dehydrocyclization of Alkanes Over Zeolite-Supported Metal Catalysts: Monofunctional or Bifunctional Route", Catalysts Reviews, vol. 39, pp. 5-48, 1977.
Ono, "Transformation of Lower Alkanes into Aromatic Hydrocarbons over ZSM-5 Zeolites", Catalysts Reviews, Science and Engineering, vol. 34, pp. 179-226, 1992.
Su et al., "Synergic Effect of GaO+/Bronsted Acid in Hierarchical Ga/Al-ZSM-5 Bifunctional Catalysts for 1-Hexene Aromatization", Industrial & Engineering Chemistry Research, vol. 58, pp. 20543-20552, 2019.
Tamiyakul et al., "Generation of reductive Zn species over Zn/HZSM-5 catalysts for n-pentane aromatization", Applied Catalystis A: General, vol. 525, pp. 190-196, 2016.
Tshabalala et al., "Aromatizatin of n-hexane over Ga, Mo and Zn modified H-ZSM-5 zeolite catalyst", Catalysis Communications, vol. 72, pp. 49-52, 2015.
Verboekend et al., "Full Compositional Flexibility in the Preparatijn of Mesoporous MFI Zeolites by Desilication", The Journal of Physical Chemistry, 48 pgs., 2011.
Wannapakdee et al., "Aromatization of C5 hydrocarbons over Ga-modified hierarchical HZSM-5 nanosheets", Fuel, vol. 236, pp. 1243-1253, 2019.
Youming et al., "Aromatization of Methanol over La/Zn/HZSM-5 Catalysts", Catalysis, Kinetics and Reactors, Chinese Journal of Chemical Engineering, vol. 19, No. 3, pp. 439-445, 2011.
U.S. Office Action dated Sep. 29, 2021 pertaining to U.S. Appl. No. 17/011,008, filed Sep. 3, 2020, 20 pages.
Hidalgo et al., Current uses and trends in catalytic isomerization, alkylation and etherification processes to improve gasoline quality, Central European Journal of Chemistry, vol. 12, No. 1, pp. 1-13, 2014.
Yu et al., "Alkane Activation Initiated by Hydride Transfer: Co-conversion of Propane and Methanol over H-ZSM-5 Zeolite", Angew. Chem. Int. Ed. No. 54, pp. 7363-7366, 2015.
U.S. Office Action dated Mar. 1, 2022 pertaining to U.S. Appl. No. 17/011,008, filed Sep. 3, 2020, 18 pages.
Kanai, J. et al., "Aromatization of N-hexane over ZnOH-ZSM-5 catalysts", Journal of Catalysis, vol. 114, Issue 2, Dec. 1988, abstract only.
U.S. Office Action dated Mar. 31, 2022 pertaining to U.S. Appl. No. 17/338,863, filed Jun. 4, 2021, 18 pages.
International Search Report and Written Opinion dated Nov. 26, 2021 pertaining to International application No. PCT/US2021/048630 filed Sep. 1, 2021, 15 pages.
Agaeva, S. B. et al. "Product Control in Catalytic Aromatization of C2+ Hydrocarbons", Petroleum Chemistry, vol. 47, No. 3, May 1, 2007, pp. 162-166.
Tuktin, Balga Tuktievich et al. "Catalytic Conversion of Light Hydrocarbons into Aromatic Hydrocarbons over Modified Zeolite Catalysts", Oriental Journal of Chemistry, vol. 33, No. 4, Aug. 28, 2017, pp. 1799-1804.
Ellouh, Mohammed et al. "Light Paraffinic Naphtha to BTX Aromatics over Metal-Modified Pt/ZSM-5", Chemistryselect, vol. 5, No. 44, Nov. 30, 2020, pp. 13807-13813.
International Search Report and Written Opinion dated Dec. 2, 2021 pertaining to International application No. PCT/US2021/048789 filed Sep. 2, 2021, 13 pages.
Ogunronbi, K.E. et al. "New insights into hierarchical metal-containing zeolites; synthesis and kinetic modelling of mesoporous gallium-containing ZSM-5 for propane aromatization" Journal of Molecular Catalysis a Chemical, vol. 406, Sep. 1, 2015, pp. 1-18.
U.S. Office Action dated Feb. 3, 2023 pertaining to U.S. Appl. No. 17/939,281, filed Sep. 7, 2022, pp. 1-19.
Nowak et al., "Effect of H2-O2 pre-treatments on the state of fallium in Ga/H-ZSM-5 propane aromatisation catalysts", Applied Catalysis A: General 251, (2003), pp. 107-120.
Oseke et al., "Increasing the catalytic stability of microporous Zn/ZSM-5 with copper for enhanced propane aromatization", Journal of King Saud University—Engineering Sciences 33, (2021), pp. 531-538.

* cited by examiner

AROMATIZATION OF LIGHT HYDROCARBONS USING METAL-MODIFIED ZEOLITE CATALYSTS

TECHNICAL FIELD

The present disclosure generally relates to processing hydrocarbons and, more particularly, to aromatizing hydrocarbons using a metal-modified ZSM-5 zeolite catalyst.

BACKGROUND

Light hydrocarbon feedstocks, such as naphtha, may be converted to greater value chemical products, such as aromatic compounds, through various chemical reactions. Typical hydrocarbon feedstocks contain a broad range of paraffinic, olefinic, naphthenic, and aromatic hydrocarbons that must undergo one or more chemical conversions before the greater value products are obtained. One such reaction is aromatization in which non-aromatic hydrocarbons are converted to aromatic hydrocarbons, such as benzene, toluene, ethylbenzene, and xylenes, which may be collectively referred to as "BTEX." These aromatic hydrocarbon compounds may be valuable intermediates for producing plastics, fibers, or other synthetic products.

BRIEF SUMMARY

Supported catalyst compositions, such as metal oxides supported on zeolite supports, play an integral role in hydrocarbon conversion processes. Although catalysts for aromatizing hydrocarbons are known, such catalysts may suffer from relatively low yields of monoaromatic products, such as benzene, ethylbenzene, toluene, and xylenes, while also producing undesirable light gases.

Accordingly, there is a need for catalyst compositions and processes for aromatizing hydrocarbons with improved catalyst compositions to produce various greater value chemical products, such as aromatic hydrocarbon compounds. The catalyst compounds and processes of the present disclosure may include catalyst compositions including at least two different metal modifiers dispersed on surfaces of a hydrogen-form medium pore zeolite support. The medium pore size of the zeolite support and the high levels of dispersion of the metal modifiers over the surfaces of the support increase selectivity toward monoaromatic compounds while reducing the yield of less valuable light gases. The unique micropore structure and acid site distribution of the zeolite support along with the metal modifiers of the present disclosure may provide similar or even improved yield of aromatic hydrocarbon compounds from conversion of hydrocarbons through aromatization compared to existing supported catalyst compositions.

According to one or more embodiments of the present disclosure, a process for aromatizing hydrocarbons comprises contacting the hydrocarbons with a catalyst comprising at least two different metal modifiers dispersed on surfaces of a hydrogen-form medium pore size zeolite support. Each of the at least two different metal modifiers is a metal selected from the group consisting of IUPAC Groups 3-12 and lanthanide metals. The catalyst is substantially free of gallium. Contacting the hydrocarbons with the catalyst causes at least a portion of the hydrocarbons to undergo a chemical reaction to form aromatic hydrocarbons.

Additional features and advantages of the technology disclosed in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Figure 1A:
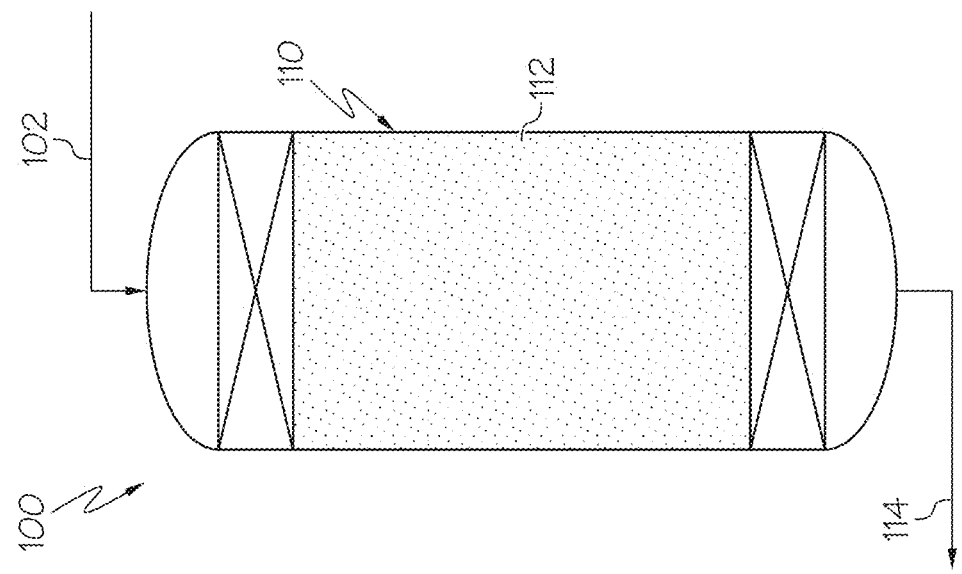
FIG. 1A schematically depicts an upflow fixed bed continuous flow reactor, according to one or more embodiments of the present disclosure.

Embodiments of the present disclosure are directed to processes for aromatizing hydrocarbons by contacting the hydrocarbons with a catalyst including at least two different metal modifiers dispersed on surfaces of a hydrogen-form medium-pore zeolite support. Each of the at least two different metal modifiers comprises a metal selected from the group consisting of IUPAC Groups 3-12, and lanthanide metals, and the catalyst is substantially free of gallium. Contacting the hydrocarbons with the catalyst causes at least a portion of the hydrocarbons to undergo chemical reactions to form aromatic hydrocarbons. As such, the processes for converting hydrocarbons to aromatic hydrocarbon compounds using the catalyst composition of the present disclosure may produce similar or even greater yields of aromatic compounds compared to conversion processes using existing supported catalyst compositions.

It should be understood that the hydrocarbon feed may be named for its components, and the component for which the feed is named may be the major component of the hydrocarbon feed (such as comprising from 50 weight percent (wt. %), from 70 wt. %, from 90 wt. %, from 95 wt. %, from 99 wt. %, from 99.5 wt. %, or even from 99.9 wt. % of the contents of the hydrocarbon feed to 100 wt. % of the contents of the feed).

As used throughout the present disclosure, the term "catalyst" may refer to any substance that increases the rate of a particular chemical reaction. Catalyst compositions described in the present disclosure may be utilized to promote various reactions, such as the aromatization of non-aromatic hydrocarbons.

As used throughout this disclosure, "zeolites" may refer to micropore-containing inorganic materials with regular intra-crystalline cavities and channels of molecular dimension. Zeolites generally comprise a crystalline structure, as opposed to an amorphous structure such as what may be observed in some porous materials such as amorphous silica. Zeolites generally include a microporous framework which may be identified by a framework type. The microporous structure of zeolites (e.g., 0.3 nm to more than 1 nm pore size) may render large surface areas and desirable size-/shape-selectivity, which may be advantageous for catalysis. The zeolites described are crystalline aluminosilicates that may additionally include metals other than silicon and aluminum. In embodiments, the zeolites described may include micropores (present in the microstructure of a zeolite). As used throughout this disclosure, micropores refer to pores in a structure that have a diameter of less than or equal to 2 nm and greater than or equal to 0.1 nm, and mesopores refer to pores in a structure that have a diameter of greater than 2 nm and less than or equal to 50 nm. Unless otherwise described herein, the "pore size" of a material refers to the average pore size, but materials may additionally include mesopores having a particular size that is not identical to the average pore size.

As used here, a "medium pore size zeolite" is a zeolite having a pore size of about 5-8 Å (0.5 to 0.8 nanometers (nm)). Suitable medium pore size zeolites are zeolites with "10-member ring" pore openings. As used herein, the term "10-member ring zeolites" refers to a zeolite in which the pore opening is formed by a ring consisting of 10 SiO4 tetrahedra.

Referring now to the process for aromatizing hydrocarbons, the process may include contacting hydrocarbons from a hydrocarbon feed with the catalyst composition of the present disclosure, which includes at least two metal modifiers dispersed on the surfaces of a hydrogen-form medium pore size zeolite support. The hydrocarbon feed may include but is not limited to alkanes, alkenes, alkynes, cycloalkanes, alkadienes, or combinations of these hydrocarbons. In embodiments, the hydrocarbons may include paraffins, olefins, naphthenes, alkylbenzenes, or combinations of these hydrocarbons. The hydrocarbons in the hydrocarbon feed may have from 1 carbon atom to 30 carbon atoms, such as from 1 carbon atom to 20 carbon atoms, from 1 carbon atom to 15 carbon atoms, from 1 carbon atom to 10 carbon atoms, from 2 carbon atoms to 30 carbons atoms, from 2 carbon atoms to 20 carbon atoms, from 2 carbon atoms to 15 carbon atoms, from 2 carbon atoms to 12 carbon atoms, from 1 to 10 carbon atoms, from 4 carbon atoms to 20 carbon atoms, from 4 carbon atoms to 10 carbon atoms, or from 3 carbon atoms to 6 carbon atoms. For example, and not by way of limitation, the hydrocarbon feed to be contacted with the catalyst composition may include one or more of methane, ethane, ethene, ethyne, propane, propene, propyne, butane, butene, butyne, pentane, pentene, pentyne, hexane, hexene, hexyne, cyclohexane, cyclohexene, heptane, heptene, heptyne, octane, octene, octyne, nonane, nonene, nonyne, and combinations of these hydrocarbons.

The hydrocarbon feed may include one or more intermediate streams from a hydrocarbon processing facility, such as but not limited to light naphtha, heavy naphtha, or combinations of these. In embodiments, the hydrocarbons feed may include straight run light naphtha. As used herein, "straight run light naphtha" refers to a distillation cut from crude oil being made up of pentane and slightly heavier naphtha range material. In one or more embodiments, the hydrocarbon feed may include light naphtha comprising at least 50 wt. % alkanes and having a boiling point temperature of from 30 degrees Celsius (° C.) to 90° C., based on the total weight of the hydrocarbon feed. In one or more embodiments, the hydrocarbon feed may include from 50 wt. % to 99.9 wt. % alkanes, from 55 wt. % to 99.9 wt. % alkanes, from 60 wt. % to 99.9 wt. % alkanes, from 65 wt. % to 99.9 wt. % alkanes, from 70 wt. % to 99.9 wt. % alkanes, or from 75 wt. % to 99.9 wt. % alkanes, based on the total weight of the hydrocarbon feed. In one or more embodiments, the hydrocarbon feed may include from 50 wt. % to 99.9 wt. % $C_5$ and $C_6$ hydrocarbons, such as from 55 wt. % to 99.9 wt. % $C_5$ and $C_6$ hydrocarbons, from 60 wt. % to 99.9 wt. % $C_5$ and $C_6$ hydrocarbons, from 65 wt. % to 99.9 wt. % $C_5$ and $C_6$ hydrocarbons, from 70 wt. % to 99.9 wt. % $C_5$ and $C_6$ hydrocarbons, or from 75 wt. % to 99.9 wt. % $C_5$ and $C_6$ hydrocarbons, based on the total weight of the hydrocarbon feed. In embodiments, the hydrocarbon feed may include aromatic, naphthenic, or aromatic and naphthenic hydrocarbons in minor amounts by volume.

The catalyst composition may include at least two metal modifiers dispersed on the surfaces of the zeolite support. The catalyst composition may include salts of a metal selected from Groups 3-12, and lanthanide groups of the International Union of Pure and Applied Chemistry (IUPAC) periodic table. In one or more embodiments, at least one of the metal modifiers is a metal selected from the group consisting of IUPAC Groups 3-12 metals. The metal may include, but is not limited to, zinc (Zn), chromium (Cr), manganese (Mn), platinum (Pt), iron (Fe), molybdenum (Mo), or combinations of these metals. In one or more embodiments, at least one of the metal modifiers is a metal of the lanthanide group. The metal may include, but is not limited to, lanthanum (La) and cerium (Ce). In embodiments, at least one of the metal modifiers is Zn, Cr, Mn, Pt, Fe, or Mo and another of the metal modifiers is La or Ce. For example, in embodiments, Zn and La, Pt and Zn, or Mo and Zn are dispersed on the surfaces of the zeolite support. In embodiments, the catalyst is substantially free of gallium. As used herein, the phrase "substantially free of gallium" means there is less than 0.05 wt. % of gallium present in the catalyst. In embodiments, the catalyst is free of gallium. Such catalysts, however, may exhibit a comparable or even enhanced yield of aromatics as compared to traditional gallium-based MFI catalysts.

The metal modifiers may be incorporated into the catalyst as metal precursors or metal salts, such as oxides, nitrates, acetates, and sulphates. In embodiments, the metal modifier may be incorporated into the catalyst as a nitrate nonahydrate, a nitrate hexahydrate, a nitrate, a nitrate hydrate, an oxide, or the like. Suitable metal modifiers can include, by way of example and not limitation, chromium (III) nitrate nonahydrate, cerium (III) nitrate hexahydrate, tetra-amine-platinum (II) nitrate, iron (III) nitrate nonahydrate, zinc nitrate hexahydrate, and lanthanum (III) nitrate hydrate.

The at least two metal modifiers may be dispersed on the surfaces of the zeolite support. The surfaces of the zeolite support may include the outer surfaces of the zeolite support as well as the surfaces of the pores extending into the zeolite support. The catalyst composition may include an amount of the metal modifiers dispersed on the surfaces of the zeolite support that is sufficient to cause at least a portion of the hydrocarbons to undergo a chemical reaction to form aromatic hydrocarbons. The catalyst composition may include from 0.1 wt. % to 20 wt. % of each metal modifier, based on the total weight of the catalyst composition. For example, the catalyst composition may include from 1 wt. % to 20 wt. %, from 1 wt. % to 18 wt. %, from 1 wt. % to 15 wt. %, from 1 wt. % to 10 wt. %, from 2 wt. % to 20 wt. %, from 2 wt. % to 18 wt. %, from 2 wt. % to 15 wt. %, or from 2 wt. % to 10 wt. %, based on the total weight of the catalyst composition.

The zeolite support may include MFI zeolites, MEL zeolites, MWW zeolites, FER zeolites, or combinations of these zeolite types. Framework types are described in, for example, "Atlas of Zeolite Framework Types" by Ch. Baerlocher et al, Fifth Revised Edition, 2001, the teachings of which are incorporated by reference herein. It should be understood that MFI, MEL, MWW, and FER refer to zeolite framework types as identified by its three letter code established by the International Union of Pure and Applied Chemistry (IUPAC). Other framework types are contemplated in the presently disclosed embodiments.

In embodiments, the zeolite support may be a ZSM-5 zeolite. "ZSM-5" generally refers to zeolites having an MFI framework type according to the IUPAC zeolite nomenclature and consisting majorly of silica and alumina, as is understood by those skilled in the art. ZSM-5 refers to "Zeolite Socony Mobil-5" and is a pentasil family zeolite that can be represented by the chemical formula $Na_nAl_nSi_{96-n}O_{192}\cdot 16H_2O$, where $0<n<27$. In embodiments, the zeolite support may be a medium pore size ZSM-5 zeolite.

The aromatization of hydrocarbons is a multi-step reaction involving cracking, oligomerization, isomerization, and cyclization at Brønsted acid sites and the dehydrogenation and/or hydrogen transfer at the Lewis acid sites. Accordingly, in embodiments, the zeolite may be in protonic form (i.e., hydrogen-form). A zeolite in protonic form provides Brønsted acid sites and some Lewis acid sites required for aromatization reaction. The acidity of the zeolite catalyst can be quantitatively determined by the ammonia temperature-programmed desorption ($NH_3$-TPD) method described in ASTM D4824-13. In various embodiments, the zeolite support is a hydrogen-form medium pore size zeolite support, such as hydrogen form ZSM-5, or HZSM-5.

In embodiments, zeolite support has a molar ratio of silica to alumina of at least 5:1. For example, the molar ratio of silica to alumina in the zeolite may be at least at least 5:1, 10:1, at least 12:1, at least 23:1, or even at least 30:1, such as from 5:1 to 300:1, from 12:1 to 250:1, from 23:1 to 200:1, or from 23:1 to 80:1. In embodiments, the molar ratio of silica to alumina of the zeolite support may range from 5:1 to 300:1, from 15:1 to 300:1, from 23:1 to 300:1, from 30:1 to 300:1, from 5:1 to 250:1, from 15:1 to 250:1, from 23:1 to 250:1, from 30:1 to 250:1, from 5:1 to 200:1, from 15:1 to 200:1, from 23:1 to 200:1, from 30:1 to 200:1, from 5:1 to 150:1, from 15:1 to 150:1, from 23:1 to 150:1, from 30:1 to 150:1, from 5:1 to 100:1, from 15:1 to 100:1, from 23:1 to 100:1, from 30:1 to 100:1, from 5:1 to 80:1, from 15:1 to 80:1, from 23:1 to 80:1, from 30:1 to 80:1, from 5:1 to 50:1, from 15:1 to 50:1, from 23:1 to 50:1, from 30:1 to 50:1, from 5:1 to 45:1, from 15:1 to 45:1, from 23:1 to 45:1, from 30:1 to 45:1, from 5:1 to 40:1, from 15:1 to 40:1, from 23:1 to 40:1, or from 30:1 to 40:1.

As described above, the catalyst composition may include the metal modifiers dispersed across the outer surfaces and pore surfaces of the zeolite support. In one or more embodiments, the catalyst composition may consist of or consist essentially of the metal modifiers dispersed onto the outer surfaces and pore surfaces of the zeolite support. The catalyst composition may have a BET surface area of from 100 square meters per gram ($m^2/g$) to 600 $m^2/g$, such as from 150 $m^2/g$ to 550 $m^2/g$, from 200 $m^2/g$ to 500, from 250 $m^2/g$ to 450 $m^2/g$, from 300 $m^2/g$ to 400 $m^2/g$, from 305 $m^2/g$ to 390 $m^2/g$, from 310 $m^2/g$ to 380 $m^2/g$, from 310 $m^2/g$ to 370 $m^2/g$, from 310 $m^2/g$ to 360 $m^2/g$, from 310 $m^2/g$ to 350 $m^2/g$, from 310 $m^2/g$ to 340 $m^2/g$, from 310 $m^2/g$ to 330 $m^2/g$, or from 310 $m^2/g$ to 320 $m^2/g$. The catalyst composition may have an average pore diameter of from 4.0 nanometers (nm) to 50.0 nm, such as from 4.0 nm to 40.0 nm, from 4.0 nm to 30.0 nm, from 4.0 nm to 20.0 nm, from 4.0 nm to 10.0 nm, from 4.0 nm to 9.0 nm, from 4.0 nm to 8.0 nm, from 4.0 nm to 7.5 nm, from 4.0 nm to 7.0 nm, from 4.0 nm to 6.0 nm, from 4.0 nm to 5.5 nm, from 4.1 nm to 50.0 nm, from 4.1 nm to 40.0 nm, from 4.1 nm to 30.0 nm, from 4.1 nm to 20.0 nm, from 4.1 nm to 10.0 nm, from 4.1 nm to 9.0 nm, from 4.1 nm to 8.0 nm, from 4.1 nm to 7.5 nm, from 4.1 nm to 7.0 nm, from 4.1 nm to 6.0 nm, from 4.1 nm to 5.5 nm, from 4.3 nm to 50.0 nm, from 4.3 nm to 40.0 nm, from 4.3 nm to 30.0 nm, from 4.3 nm to 20.0 nm, from 4.3 nm to 10.0 nm, from 4.3 nm to 9.0 nm, from 4.3 nm to 8.0 nm, from 4.3 nm to 7.5 nm, from 4.3 nm to 7.0 nm, from 4.3 nm to 6.0 nm, from 4.3 nm to 5.5 nm, from 4.5 nm to 50.0 nm, from 4.5 nm to 40.0 nm, from 4.5 nm to 30.0 nm, from 4.5 nm to 20.0 nm, from 4.5 nm to 10.0 nm, from 4.5 nm to 9.0 nm, from 4.5 nm to 8.0 nm, from 4.5 nm to 7.5 nm, from 4.5 nm to 7.0 nm, from 4.5 nm to 6.0 nm, or from 4.5 nm to 5.5 nm.

The catalyst composition may have a pore volume of greater than 0.100 $cm^3/g$. In embodiments, the catalyst composition may have pore volume of greater than or equal to 0.110 $cm^3/g$, greater than or equal to 0.120 $cm^3/g$, greater than or equal to 0.130 $cm^3/g$, greater than or equal to 0.140 $cm^3/g$, greater than or equal to 0.150 $cm^3/g$, greater than or equal to 0.160 $cm^3/g$, greater than or equal to 0.170 $cm^3/g$, greater than or equal to 0.180 $cm^3/g$, greater than or equal to 0.190 $cm^3/g$, or even greater than or equal to 0.20 $cm^3/g$, and less than or equal to 0.250 $cm^3/g$.

Surface area, average pore size, and pore volume distribution may be measured by $N_2$ adsorption isotherms performed at 77 Kelvin (K) (such as with a Micrometrics ASAP 2020 system). As would be understood by those skilled in the art Brunauer, Emmett, and Teller (BET) analysis methods may be utilized.

In embodiments, the crystalline particles of the zeolite support have a "crystal size" measured by powder X-ray diffraction (XRD) method. The zeolite crystalline particles may have a crystal size from 25 nm to 500 nm, from 50 nm to 400 nm, from 100 nm to 300 nm, or less than 900 nm, less than 800 nm, less than 700 nm, less than 600 nm, less than 500 nm, less than 400 nm, less than 300 nm, or less than 250 nm.

The catalyst composition may be formed as an assembly of zeolite crystals. The crystalline structure of the catalyst composition may have a branched, fibrous structure with highly interconnected intra-crystalline pores. Such structures may be advantageous in applications where the structural integrity of the catalyst composition is important while the ordering of the mesopores is not.

The zeolite support may be doped with the metal modifiers in the form of a metal precursor or metal salt to form the catalyst. Doping of the zeolite support can be conducted using any one of a variety of processes known and used in the art, including, but not limited to, impregnation, ion-exchange, precipitation, chemical fusion, or chemical vapor deposition.

Aromatization catalyst compositions that are formed for aromatization of light naphthas described herein comprise an effective amount of one or more inorganic oxide components, an effective amount of one or more zeolite components as described herein, and in certain embodiments an effective amount of one or more active components.

The inorganic oxide component excludes the herein zeolite, and typically contains a substance serving as a granulating agent or a binder. Usually, a known substance can be used as a granulating agent or binder for the aromatization catalyst herein. As the inorganic oxide, a porous inorganic oxide used in aromatization catalyst compositions in the related art can be used. Examples thereof include alumina, silica, titania, silica-alumina, alumina-titania, alumina-zirconia, alumina-boria, phosphorus-alumina, silica-alumina-boria, phosphorus-alumina-boria, phosphorus-alumina-silica, silica-alumina-titania, and silica-alumina-zirconia. In certain embodiments of the process for aromatization of light naphtha as described herein, an inorganic oxide component comprising alumina, silica-alumina or a combination of alumina and silica-alumina is used in the aromatization catalyst compositions.

The catalyst extrudate may be in the form of cylinder, trilobe, quadralobe, or spheres for fixed-bed reactor configurations or spray dried particles for fluidized-bed configuration.

In embodiments, the zeolite content of the catalyst composition may be in the range 1-80 wt. % based on a total weight of the catalyst composition.

The catalyst composition of the present disclosure may be utilized in a process to convert hydrocarbons to one or more aromatic compounds. The process of the present disclosure for aromatizing hydrocarbons may include contacting hydrocarbons with a catalyst composition comprising at least two different metal modifiers dispersed on a surface of a hydrogen-form medium pore size zeolite support within a catalyst system, where contacting the hydrocarbons with the catalyst composition causes at least a portion of the hydrocarbons to undergo chemical reactions to form aromatic hydrocarbons. The process for converting hydrocarbons to aromatic compounds may further include pretreating the catalyst composition formed according to any of the previously described embodiments. Pretreating the catalyst composition may improve the catalyst composition's ability to aromatize hydrocarbons. The catalyst composition may be pretreated under nitrogen and/or hydrogen flow at a temperature from 400° C. to 700° C. For example, the pretreatment temperature may be from 425° C. to 700° C., from 450° C. to 700° C., from 475° C. to 700° C., from 500° C. to 700° C., from 525° C. to 700° C., from 550° C. to 700° C., from 400° C. to 675° C., from 400° C. to 650° C., from 400° C. to 625° C., from 400° C. to 600° C., from 425° C. to 675° C., from 450° C. to 650° C., from 475° C. to 625° C., from 500° C. to 600° C., or from 525° C. to 575° C. The pretreatment of the catalyst composition may be conducted for a duration from 1.0 hour to 5.0 hours, such as from 1.5 hours to 5.0 hours, from 2.0 hours to 5.0 hours, from 2.5 hours to 5.0 hours, from 1.0 hour to 4.5 hours, from 1.0 hour to 4.0 hours, from 1.0 hour to 3.5 hours, from 1.5 hours to 4.5 hours, from 2.0 hours to 4.0 hours, or from 2.5 hours to 3.5 hours.

Following pretreatment of the catalyst composition, the hydrocarbon feed may be contacted with the catalyst composition under reaction conditions sufficient to cause at least a portion of the hydrocarbons to undergo chemical reactions to form aromatic hydrocarbons. The contacting may occur within a catalyst system and will now be described.

Figure 1B:
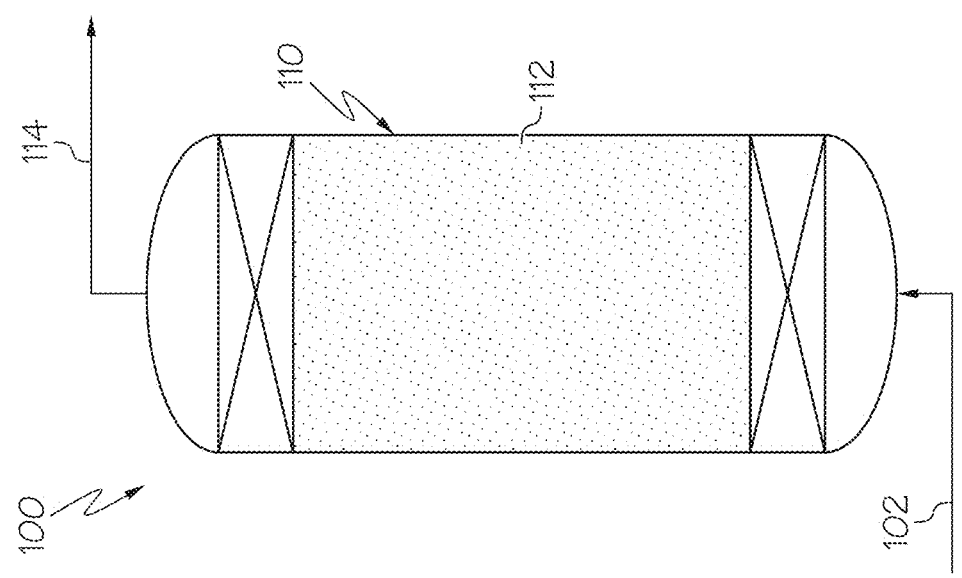
FIG. 1B schematically depicts a downflow fixed bed continuous flow reactor, according to one or more embodiments of the present disclosure.

Referring now to FIGS. 1A and 1B, an embodiment of the catalyst system for producing aromatic hydrocarbons from a hydrocarbon feed containing non-aromatic hydrocarbons is illustrated, the catalyst system being designated by reference number 100. In FIG. 1A, the catalyst system 100 is configured as an upflow reactor, while in FIG. 1B, the catalyst system 100 is configured as a downflow reactor. The catalyst system 100 may include a reaction zone 110. In one or more embodiments, the reaction zone 110 may be a portion of a reactor that includes the catalyst composition 112 of the present disclosure. The catalyst system 100 may include one or a plurality of reactors. The reactor or reactors of the catalyst system 100 may include but are not limited to tank or tubular reactors, which may be configured to operate as a batch reactor, a fixed-bed reactor, a continuous stirred-tank reactor (CSTR), or a plug flow reactor. As depicted in FIGS. 1A and 1B, the hydrocarbon feed 102 including one or more non-aromatic hydrocarbons may be introduced to the reaction zone 110, and reactor effluent 114 may be passed out of the reaction zone 110 following contact of the hydrocarbons of the hydrocarbon feed 102 with the catalyst composition 112 in the reaction zone 110. Contacting the hydrocarbons present in the hydrocarbon feed 102 with the catalyst composition 112 in the reaction zone 110 may cause at least a portion of the hydrocarbons from the hydrocarbon feed 102 to undergo a chemical reaction to form aromatic hydrocarbons, which may be present in the reactor effluent 114. The reactor effluent 114 comprising the aromatic hydrocarbons may be passed out of the reaction zone 110.

The hydrocarbon feed 102 may be contacted with the catalyst composition 112 in the reaction zone 110 under reaction conditions sufficient to cause at least a portion of the hydrocarbons to undergo a chemical reaction to form aromatic hydrocarbons. The hydrocarbon feed 102 may be contacted with the catalyst composition 112 in the reaction zone 110 at a reaction temperature from 200° C. to 900° C., such as from 250° C. to 850° C., from 300° C. to 800° C., from 350° C. to 750° C., from 400° C. to 700° C., from 450° C. to 650° C., from 475° C. to 625° C., from 500° C. to 600° C., from 525° C. to 575° C., or at 550° C. The hydrocarbon feed 102 may be contacted with the catalyst composition 112 in the reaction zone 110 at a pressure from 1 bar to 30 bars, such as from 1 bar to 25 bars, from 1 bar to 20 bars, from 1 bar to 15 bars, from 1 bar to 10 bars, or at 5 bars. The hydrocarbon feed 102 may be contacted with the catalyst composition 112 in the reaction zone 110 at a weight hourly space velocity (WHSV) from 0.1 per hour to 20.0 per hour, such as from 0.25 per hour to 15.0 per hour, from 0.5 per hour to 10.0 per hour, from 0.75 per hour to 5.0 per hour, from 0.75 per hour to 2.0 per hour, or from 0.75 per hour to 1.25 per hour.

The reactor effluent 114 may include one or a plurality of aromatic hydrocarbons, such as but not limited to benzene, toluene, ethylbenzene, mixed xylenes (ortho-xylene, meta-xylene, para-xylene, or mixtures of these), and combinations of such hydrocarbons. In embodiments, after contacting the hydrocarbon feed with the catalyst composition, the hydrocarbons comprise aromatic hydrocarbons in major proportions and naphthenic hydrocarbons in minor proportions by volume.

Benzene, toluene, ethylbenzene, and mixed xylenes may be collectively referred to as "BTEX." In one or more than one embodiment, at least 70% by weight of the hydrocarbons from the hydrocarbon feed undergo a chemical reaction to form aromatic hydrocarbons, such as at least 70.5%, at least 71%, at least 71.5%, at least 72%, at least 72.5%, at least 73%, at least 73.5%, at least 74%, at least 74.5%, or at least 75% by weight. In embodiments, 100% of the hydrocarbons undergo the chemical reactions to form aromatic hydrocarbons. In one or more embodiments, at least 60% by weight of the hydrocarbons undergo chemical reactions to form BTEX hydrocarbons, such as at least 60.25%, at least 60.5%, at least 60.75%, at least 61%, at least 61.25%, at least 61.5%, at least 61.75%, at least 62%, at least 62.25%, at least 62.5%, at least 62.75%, or at least 63% by weight. In embodiments, the process yields greater than or equal to 45%, greater than or equal to 50%, greater than or equal to 55%, greater than or equal to 60%, greater than or equal to 65%, or greater than or equal to 70% by weight of aromatic hydrocarbons.

EXAMPLES

The following examples illustrate one or more additional features of the present disclosure described previously. It should be understood that these examples are not intended to limit the scope of the disclosure or the appended claims in any manner.

In the following examples, aromatization catalyst compositions were prepared according to a variety of techniques and characterized for the suitability for aromatizing hydrocarbons.

Example 1

A hydrotreated light straight run (LSR) naphtha was received from a refinery processing 75% (volume) Arab heavy crude oil and 25% (volume) Arab light crude oil. The hydrotreated LSR naphtha feed contained 43 ppm sulfur and had a density of 0.6764 g/cm$^3$. The content of LSR naphtha for n-paraffin, iso-paraffins, olefins, naphthenes, and aromatics (PIONA) was analyzed using a Shimadzu gas chromatograph fitted with detailed hydrocarbon analysis (GC-DHA) using a flame ionization detector (FID) and a thermal conductivity detector (TCD) employing an Rtx-PONA, 100 m×0.25 mm×0.5 μm with the oven temperature programmed from 30° C. to 250° C. The results of the PIONA composition study are presented in Table 1, with the values presented in weight percent (wt. %).

TABLE 1

Results of PIONA composition of hydrotreated LSR naphtha feed.

| Component | n-Paraffins | Iso-Paraffins | Olefins | Naphthenes | Aromatics | Total |
|---|---|---|---|---|---|---|
| C$_5$ | 22.5 | 8.8 | 0.0 | 2.1 | 0.0 | 36.4 |
| C$_6$ | 25.4 | 26.5 | 0.0 | 5.4 | 1.5 | 58.8 |
| C$_7$ | 0.8 | 3.3 | 0.0 | 0.6 | 0.1 | 4.8 |
| Total | 51.7 | 38.6 | 0.0 | 8.1 | 1.6 | 100.0 |

As shown in Table 1, the LSR naphtha is strongly paraffinic, with paraffins constituting over 90 wt. % of the feed.

Example 2

Various zeolite frameworks were studied to identify frameworks that exhibited a good match of microchannel diameters with kinetic diameters of the mono-aromatics. Characteristics of various zeolites are presented in Table 2, and the dimensions of aromatic products are presented in Table 3.

TABLE 2

Characteristics of zeolites.

| Type | Zeolite | IZA Framework Type | Dimensionality | Channel Type | Channel Diameter (nm) |
|---|---|---|---|---|---|
| Medium-pore zeolites | MCM-22 | MWW | 2 | 10-MR | 0.40 × 0.55, 0.41 × 0.51 |
| | ZSM-11 | MEL | 3 | 10-MR | 0.53 × 0.54 |
| | ZSM-5 | MFI | 3 | 10-MR | 0.51 × 0.55, 0.53 × 0.56 |
| Mixed-pore zeolite | Ferrierite | FER | 2 | 8-MR, 10-MR | 0.35 × 0.48, 0.42 × 0.54 |

TABLE 3

Dimensions of aromatic products.

| Component | Kinetic Diameter σ (nm) |
|---|---|
| Benzene | 0.59 |
| Toluene | 0.59 |
| p-Xylene | 0.59 |
| m-Xylene | 0.59 |
| o-Xylene | 0.68 |
| Ethyl benzene | 0.60 |
| n-Propylbenzene | 0.68 |
| i-Propylbenzene | 0.68 |

Based on the data presented in Tables 2 and 3, it was expected that the medium-pore zeolites with 10-membered-ring (10-MR) openings (e.g., ZSM-5, ZSM-11, and MCM-22), which have microchannel diameters of about 0.55 nm, would have a good match with the kinematic diameters of the mono-aromatic molecules, and would lead to unique shape selectivity toward the mono-aromatics). The zeolite with the mixed microchannel diameters (e.g., Ferrierite) was also expected to have partial shape selectivity to the mono-aromatics.

Accordingly, the catalytic performance of the medium pore size zeolite catalysts (ZSM-5, ZSM-11, and MCM-22) was evaluated. The catalyst (0.5 g) was heated to 550° C. in a nitrogen flow. While keeping a constant N$_2$ flow of 10 mL/min, the LSR naphtha feed was introduced to the reactor through a liquid syringe pump to start the reaction. The reaction was kept running at 550° C., atmospheric pressure, and weight hourly space velocity (WHSV) of 1 h$^{-1}$ for one hour. The reaction products were analyzed using the GC-DHA described in Example 1, and the results are reported in Table 4.

TABLE 4

Catalytic performance of zeolite catalysts with different framework types.

| Framework Type | MFI<br>ZSM-5 | MEL<br>ZSM-11 | MWW<br>MCM-22 |
|---|---|---|---|
| $SiO_2/Al_2O_3$ (mol:mol) | 30 | 35 | 55 |
| Conversion (%) | 99.8 | 92.8 | 67.6 |
| Yield (wt. %) | | | |
| Benzene | 15.0 | 6.2 | 5.8 |
| Toluene | 7.0 | 8.3 | 2.8 |
| Ethylbenzene | 0.0 | 0.6 | 0.0 |
| Xylene | 2.0 | 4.6 | 2.3 |
| BTEX | 24.0 | 19.7 | 10.8 |
| C9 + Arom | 7.9 | 0.5 | 0.7 |
| C5 + P&O* | 14.9 | 9.1 | 34.6 |
| Total Arom. | 31.9 | 20.2 | 11.5 |
| C1 | 4.9 | 1.9 | 0.7 |
| C2 | 3.6 | 2.7 | 1.0 |
| C2= | 1.8 | 5.6 | 2.7 |
| C3 + C4 | 42.9 | 60.5 | 49.5 |
| Total C1-C4 | 53.2 | 70.8 | 53.9 |

*P&O = Paraffins and olefins

Accordingly, as shown in Table 4, the MFI framework (ZSM-5) exhibited both the greatest conversion rate (99.8%) as well as the greatest yield of aromatics (31.9 wt. %). Therefore, for the remainder of the experiments, ZSM-5 was used as the zeolite support.

Example 3

Next, the silica to alumina ratio of the ZSM-5 catalyst was varied to determine the effect of the ratio on the selectivity of the catalyst. ZSM-5 catalysts with silica to alumina mole ratios of 23, 30, 50, 80, and 280 (0.5 g) were heated to 550° C. in a nitrogen flow. While keeping a constant $N_2$ flow of 10 mL/min, the LSR naphtha feed was introduced to the reactor through a liquid syringe pump to start the reaction. The reaction was kept running at 550° C., atmospheric pressure, and weight hourly space velocity (WHSV) of $1\ h^{-1}$ for one hour. The reaction products were analyzed using the GC-DHA described in Example 1, and the results are reported in Table 5.

TABLE 5

Catalytic performance of ZSM-5 catalysts with different $SiO_2/Al_2O_3$ mole ratios

| | ZSM-5 | ZSM-5 | ZSM-5 | ZSM-5 | ZSM-5 |
|---|---|---|---|---|---|
| $SiO_2/Al_2O_3$ (mol:mol) | 23 | 30 | 50 | 80 | 280 |
| Conversion (%) | 99.7 | 99.8 | 99 | 65.2 | 22.3 |
| Yield (wt %) | | | | | |
| Benzene | 12.6 | 15.0 | 6.0 | 2.0 | 1.5 |
| Toluene | 17.2 | 7.0 | 10.2 | 3.5 | 0.0 |
| Xylene | 7.8 | 2.0 | 7.6 | 3.3 | 0.0 |
| BTX | 37.6 | 24.0 | 23.7 | 8.8 | 1.5 |
| C9 + Arom | 0.0 | 7.9 | 0.0 | 0.0 | 4.3 |
| C5 + P&O | 0.3 | 14.9 | 1.0 | 34.8 | 77.7 |
| Total Arom. | 37.6 | 31.9 | 23.8 | 8.8 | 5.8 |
| C1 | 12.1 | 4.9 | 6.8 | 1.6 | 0.7 |
| C2 | 11.6 | 3.6 | 8.9 | 4.2 | 2.1 |
| C2= | 4.2 | 1.8 | 4.7 | 6.7 | 3.5 |
| C3 + C4 | 34.2 | 42.9 | 54.8 | 43.9 | 10.2 |
| Total C1-C4 | 62.1 | 53.2 | 75.2 | 56.4 | 16.5 |

Although the zeolite catalyst with a silica to alumina ratio of 23 shows the highest yield of aromatics (37.6 wt. %), it was deactivated very quickly due to its high acidity and coke formation compared to the zeolite catalyst with a silica to alumina ratio of 30. Accordingly, for the remainder of the experiments, ZSM-5 having a silica to alumina ratio of 30 was used as the zeolite support.

Example 4

Samples of metal-modified ZSM-5 zeolite catalysts were prepared. Metal precursors chromium (III) nitrate nonahydrate, cerium (III) nitrate hexahydrate, tetra-ammine-platinum (II) nitrate, iron(III) nitrate nonahydrate, zinc nitrate hexahydrate, and lanthanum (III) nitrate hydrate were used for incorporating chromium, cerium, platinum, iron, zinc, and lanthanum, respectively, in ZSM-5 zeolite. In particular, 5.0 grams of commercially available protonic form of ZSM-5 zeolite powder from Zeolyst, which has a silica-to-alumina molar ratio of 30, was mixed with 5.0 mL of aqueous solution containing appropriate amount of precursor nitrate(s). In particular, 0.7656 g chromium (III) nitrate nonahydrate, 0.3099 g cerium (III) nitrate hexahydrate, 0.0992 g tetra-ammine-platinum (II) nitrate, 0.7234 g iron (III) nitrate nonahydrate, 0.2275 g zinc nitrate hexahydrate, and/or 0.2340 g lanthanum (III) nitrate hydrate, respectively, were present in the various solutions, depending on the catalyst to be formed. The resulting mixture was stirred for 3 hours at room temperature. Excess water was further removed by slow evaporation of the resulting mixture at 60° C. under stirring. The product was dried overnight at 100° C. followed by calcination in a muffle furnace at 550° C. for 5 hours. For each sample, the resulting solid was pelletized, sieved to particle size of 500-1000 μm and tested in fixed-bed reactor.

Example 5

Each of the catalyst samples of Example 4 were characterized using powder X-ray diffraction (XRD), nitrogen adsorption, and scanning electron microscope (SEM).

The XRD was performed on a Rigaku Mini-flex II device with nickel-filtered CuKα radiation ($\lambda$=1.5406 Å) operated in a static scanning mode at a detector angular speed of 2° per minute and a step size of 0.02°. The resultant XRD patterns for the HZSM-5 catalyst and the metal-modified HZSM-5 catalysts are shown in FIG. 2.

Figure 2:
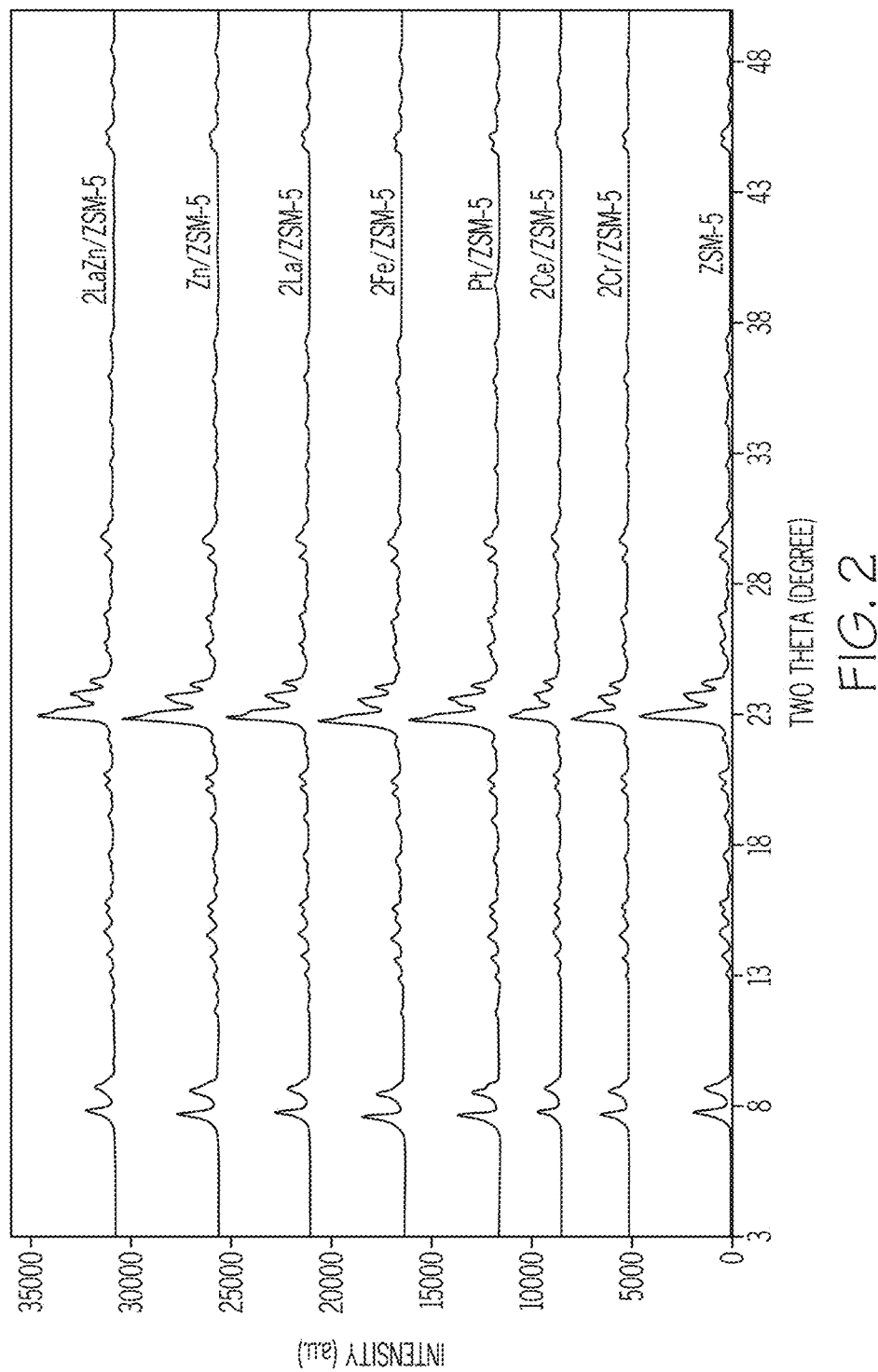
FIG. 2 depicts X-ray diffraction (XRD) spectra for a HZSM-5 catalyst and metal-modified ZSM-5 catalysts according to one or more embodiments of the present disclosure.

As shown in FIG. 2, all of the catalysts displayed characteristic diffraction lines of the ZSM-5 structure in the 2-theta ranges of 7-10° and 22-25°. The consistency of the intensities of the characteristic diffraction lines indicated that the crystallinity of the ZSM-5 structure was maintained after impregnation of the Cr, Ce, Pt, Fe, La, and Zn metal modifiers. Additionally, no crystalline metal oxide phases were identifiable in the metal-modified ZSM-5 samples, strongly suggesting that all of the metal modifiers were well-dispersed on the zeolite support, and segregation of the metal modifiers did not occur during impregnation.

The textual properties (surface area, pore volume, and pore diameter) of the HZSM-5 catalyst (Comp. A) and the metal-modified ZSM-5 catalysts 2Cr/ZSM-5 (Comp. B), 2Ce/ZSM-5 (Comp. C), Pt/ZSM-5 (Comp. D), 2Fe/ZSM-5 (Comp. E), 2La/ZSM-5 (Comp. F), Zn/ZSM-5 (Comp. G), and 2LaZn/ZSM-5 (Inv. 1) were determined by nitrogen adsorption at −195° C. using a Micromeritics ASAP-2020 analyzer. The textural characteristics of the samples are presented in Table 6.

TABLE 6

Physio-chemical properties of ZSM-5 catalysts.

| Sample ID | Catalyst | SiO$_2$/Al$_2$O$_3$ molar ratio | Surface Area (m$^2$/g) | Pore size (nm) | Pore volume (cm$^3$/g) |
|---|---|---|---|---|---|
| Comp. A | ZSM-5 | 30 | 351 | 4.68 | 0.174 |
| Comp. B | 2Cr/ZSM-5 | 30 | 317 | 5.32 | 0.157 |
| Comp. C | 2Ce/ZSM-5 | 30 | 332 | 5.66 | 0.194 |
| Comp. D | Pt/ZSM-5 | 30 | 332 | 7.83 | 0.250 |
| Comp. E | 2Fe/ZSM-5 | 30 | 338 | 5.48 | 0.182 |
| Comp. F | 2La/ZSM-5 | 30 | 306 | 4.32 | 0.120 |
| Comp. G | Zn/ZSM-5 | 30 | 341 | 5.95 | 0.200 |
| Inv. 1 | 2LaZn/ZSM-5 | 30 | 312 | 4.25 | 0.120 |

Figure 3B:
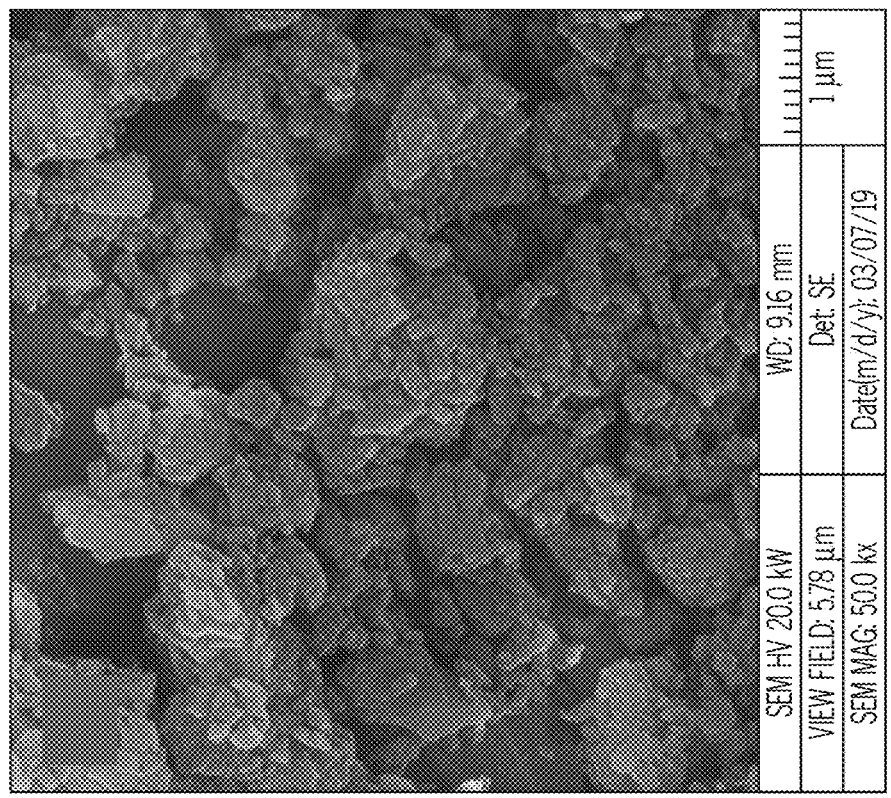
FIG. 3B is a SEM image of a ZSM-5 catalyst modified with Zn.
Figure 3A:
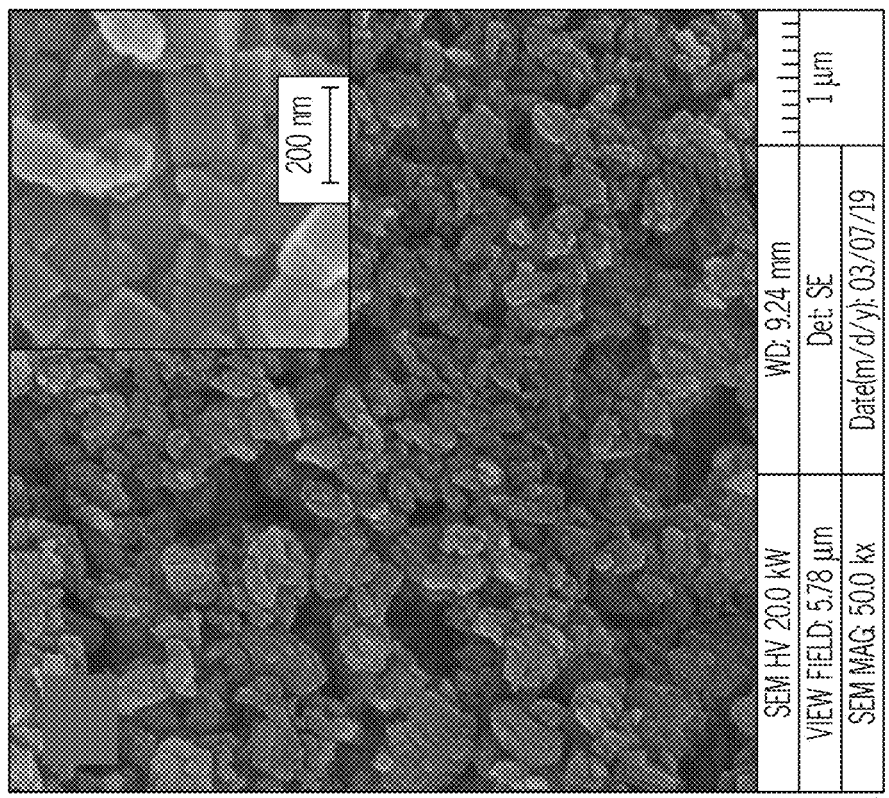
FIG. 3A is a scanning electron microscope (SEM) image of a HZSM-5 catalyst.
Figure 3D:
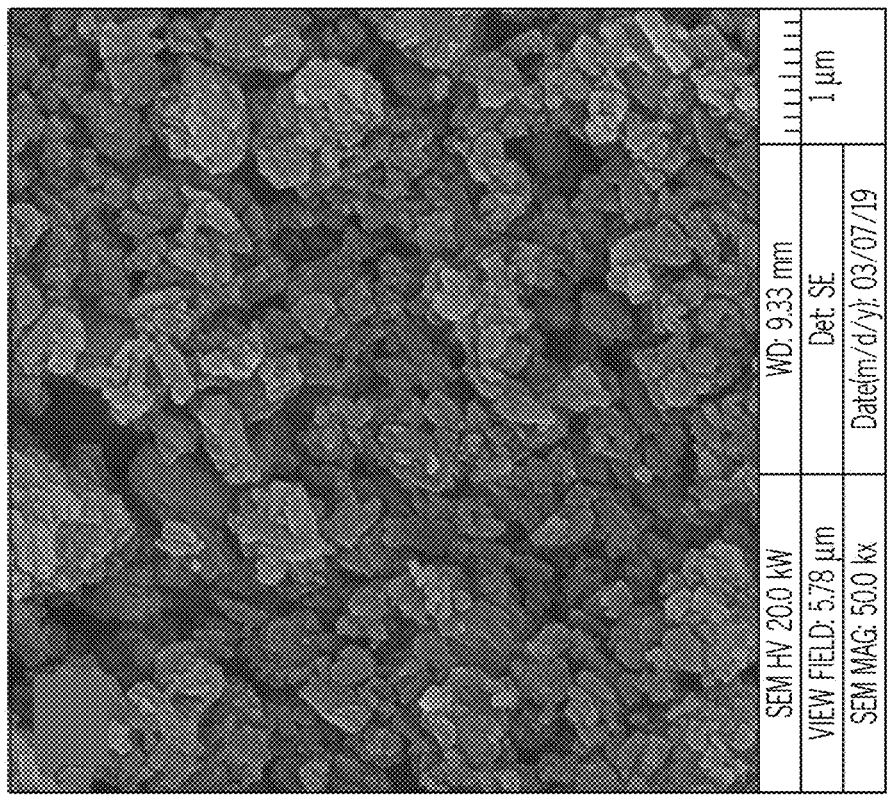
FIG. 3D is a SEM image of a ZSM-5 catalyst modified with La and Zn according to one or more embodiments of the present disclosure.
Figure 3C:
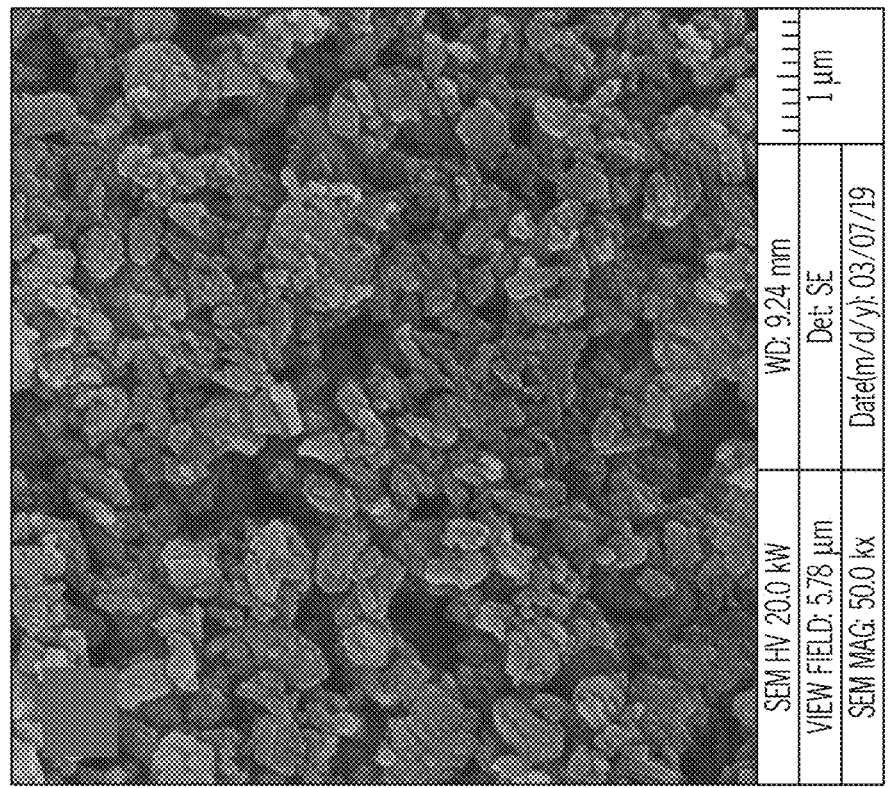
FIG. 3C is a SEM image of a ZSM-5 catalyst modified with La.

In addition, the morphological characteristics of the HZSM-5 catalyst and the metal-modified ZSM-5 catalysts were examined using an NOVA FEISEM-450 SEM equipped with an EDX detector. FIG. 3A-3D shows the SEM images of Comparative Sample A (HZSM-5 catalyst; FIG. 3A), Comparative Sample B (the ZSM-5 catalyst modified with Zn; FIG. 3B), Comparative Sample C (the ZSM-5 catalyst modified with La; FIG. 3C), and Inventive Sample 1 (ZSM-5 catalyst modified with La and Zn; FIG. 3D). As shown in FIG. 3A, Comparative Sample A has a well-ordered crystallite morphology with a broad crystal dimension with approximately less than 150 nm. In FIGS. 3B-3D, the surface morphology of the metal-modified zeolite catalysts remains unchanged even after impregnation of lanthanum, zinc, and both metals together. Additionally, elemental maps of the 2LaZn/ZSM-5 catalyst (Inv. 1) were obtained using EDXS mapping to map the dispersion of oxygen, aluminum, silicon, zinc, and lanthanum. The elemental maps confirmed the homogeneous nature of the La and Zn dispersion over the zeolite support.

Example 6

Catalyst samples were tested in a laboratory scale fixed-bed reactor using the hydrotreated LSR naphtha feed described in Example 1. For each of Comparative Samples A-H and Inventive Samples 1-3, 0.5 grams of catalyst granules with a size range of from 0.5 mm to 1.0 mm were loaded in a stainless steel tube reactor (grade 316, ø8×14 mm). The catalyst was conditioned at 550° C. in a nitrogen flow for 2 hours. While keeping a constant N$_2$ flow of 10 mL/min, the hydrotreated LSR naphtha feed was introduced to the reactor through a liquid syringe pump to start the reaction. The reaction was kept running at 550° C., atmospheric pressure, and weight hourly space velocity (WHSV) of 1.0 h$^{-1}$. The reaction products was analyzed using an online GC equipped with detailed hydrocarbons analyzer (GC-DHA). The aromatization product yields are reported in Table 7.

TABLE 7

Comparison of aromatization product yields of catalyst samples.

| | Comp. A ZSM-5 | Comp. B 2Cr/ZSM-5 | Comp. C 2Ce/ZSM-5 | Comp. D Pt/ZSM-5 | Comp. E 2Fe/ZSM-5 | Comp. F 2La/ZSM-5 |
|---|---|---|---|---|---|---|
| Conversion (%) | 99.8 | 100.0 | 99.9 | 100.0 | 94.6 | 100.0 |
| Yield (wt. %) | | | | | | |
| Benzene | 15.0 | 16.4 | 11.3 | 17.4 | 11.4 | 13.2 |
| Toluene | 7.0 | 17.5 | 15.6 | 15.4 | 10.2 | 19.2 |
| Ethylbenzene | 0.0 | 0.0 | 0.1 | 0.0 | 0.0 | 0.7 |
| Xylene | 2.0 | 2.9 | 3.4 | 1.4 | 3.1 | 9.0 |
| BTEX | 24.0 | 36.8 | 30.5 | 34.3 | 24.7 | 42.0 |
| C9 + Arom | 7.9 | 0.6 | 1.5 | 2.9 | 0.6 | 0.4 |
| C5 + P&O | 14.9 | 3.0 | 33.9 | 9.0 | 17.8 | 2.3 |
| Total Arom. | 31.9 | 37.4 | 32.0 | 37.2 | 25.2 | 42.4 |
| C1 | 4.9 | 4.2 | 6.0 | 3.6 | 2.2 | 1.9 |
| C2 | 3.6 | 3.5 | 4.3 | 8.9 | 2.8 | 2.2 |
| C2= | 1.8 | 1.6 | 1.8 | 0.7 | 2.2 | 2.2 |
| C3 + C4 | 42.9 | 50.4 | 22.1 | 40.6 | 49.8 | 49.0 |
| Total C1-C4 | 53.2 | 59.7 | 34.1 | 53.8 | 56.9 | 55.3 |

| | Comp. G Zn/ZSM-5 | Comp. H 2Mo/ZSM-5 | Inv. 1 2LaZn/ZSM-5 | Inv. 2 PtZn/ZSM-5 | Inv. 2 2MoZn/ZSM-5 |
|---|---|---|---|---|---|
| Conversion (%) | 100.0 | 100.0 | 100.0 | 100.0 | 100.0 |
| Yield (wt. %) | | | | | |
| Benzene | 25.2 | 26.5 | 26.4 | 23.3 | 23.2 |
| Toluene | 28.5 | 25.5 | 27.7 | 12.3 | 28.2 |
| Ethylbenzene | 0.0 | 0.5 | 0.1 | 0.1 | 0.3 |
| Xylene | 4.1 | 6.3 | 8.8 | 5.4 | 6.7 |
| BTEX | 57.8 | 58.7 | 63.0 | 41.1 | 58.4 |
| C9 + Arom | 0.0 | 0.5 | 0.3 | 4.0 | 3.0 |
| C5 + P&O | 0.0 | 0.0 | 0.0 | 14.1 | 0.0 |
| Total Arom. | 57.8 | 59.2 | 63.2 | 45.1 | 61.4 |
| C1 | 3.0 | 2.9 | 3.0 | 2.6 | 3.3 |
| C2 | 3.5 | 1.4 | 4.2 | 4.0 | 4.1 |
| C2= | 0.4 | 1.5 | 0.3 | 0.3 | 0.6 |
| C3 + C4 | 35.3 | 35.0 | 29.3 | 33.9 | 30.6 |
| Total C1-C4 | 42.3 | 40.8 | 36.8 | 40.9 | 38.6 |

As shown in Table 7, almost all of the catalysts show complete conversion of the LSR naphtha at 550° C. However, the results of the reactivity testing show that the hydrogen form ZSM-5 catalyst results in a total aromatics yield of 32 wt. % including 8 wt. % of C9+ aromatics. Although the aromatization performance is dramatically enhanced by using La- or Zn-modified hydrogen form ZSM-5 catalyst, which exhibited 42.4 wt. % (2La/ZSM-5) and 57.8 wt. % (Zn/ZSM-5) total aromatics yield, the 2LaZn/ZSM-5 catalyst showed the highest total aromatics yield at 63 wt. %, of which 99.6% are the BTEX monoaromatic products, with a minor 0.4% yield of C9+heavy aromatics. Moreover, the light gases yield (total C1-C4 hydrocarbons) for 2LaZn/ZSM-5 catalyst was the lowest yield. Accordingly, although the addition of a single metal modifier provides improvement, multi-metal catalysts further increase the aromatization and decrease the light gases yield.

According to a first aspect of the present disclosure, a process for aromatizing hydrocarbons comprises: contacting the hydrocarbons with a catalyst comprising at least two different metal modifiers dispersed on surfaces of a hydrogen-form medium pore size zeolite support, wherein: each of the at least two different metal modifiers comprises a metal selected from the group consisting of IUPAC Groups 3-12, and lanthanide metals; the catalyst is substantially free of gallium; and contacting the hydrocarbons with the catalyst causes a least a portion of the hydrocarbons to undergo a chemical reaction to form aromatic hydrocarbons.

According to a second aspect of the present disclosure, a process for aromatizing hydrocarbons comprises the process according to the first aspect, wherein the hydrogen-form medium pore size zeolite support has a MFI, MEL, MWW, or FER framework type.

According to a third aspect of the present disclosure, a process for aromatizing hydrocarbons comprises the process of any of the preceding aspects, wherein the hydrogen-form medium pore size zeolite support has a MFI framework type.

According to a fourth aspect of the present disclosure, a process for aromatizing hydrocarbons comprises the process of any of the preceding aspects, wherein the hydrogen-form medium pore size zeolite support is a ZSM-5 zeolite.

According to a fifth aspect of the present disclosure, a process for aromatizing hydrocarbons comprises the process of any of the preceding aspects, wherein the ZSM-5 zeolite has a silica to alumina molar ratio from 23:1 to 300:1.

According to a sixth aspect of the present disclosure, a process for aromatizing hydrocarbons comprises the process of any of the preceding aspects, wherein the ZSM-5 zeolite has a silica to alumina molar ratio from 23:1 to 80:1.

According to a seventh aspect of the present disclosure, a process for aromatizing hydrocarbons comprises the process of any of the preceding aspects, wherein a first of the at least two different metal modifiers comprises a metal selected from the group consisting of IUPAC Group 3-12 metals.

According to an eighth aspect of the present disclosure, a process for aromatizing hydrocarbons comprises the process of any of the preceding aspects, wherein the first of the at least two different metal modifiers comprises Zn, Cr, Mn, Pt, Fe, or Mo.

According to a ninth aspect of the present disclosure, a process for aromatizing hydrocarbons comprises the process of any of the preceding aspects, wherein a second of the at least two different metal modifiers comprises a metal selected from the lanthanide group.

According to a tenth aspect of the present disclosure, a process for aromatizing hydrocarbons comprises the process of any of the preceding aspects, wherein the second of the at least two different metal modifiers comprises La or Ce.

According to an eleventh aspect of the present disclosure, a process for aromatizing hydrocarbons comprises the process of any of the preceding aspects, wherein the hydrocarbons have 5 carbon atoms to 6 carbon atoms.

According to a twelfth aspect of the present disclosure, a process for aromatizing hydrocarbons comprises the process of any of the preceding aspects, wherein the hydrocarbons comprise paraffins, olefins, naphthenes, alkylbenzenes, and combinations thereof.

According to a thirteenth aspect of the present disclosure, a process for aromatizing hydrocarbons comprises the process of any of the preceding aspects, wherein each of the at least two metal modifiers is present in an amount of from 0.1 wt. % to 10 wt. %.

According to a fourteenth aspect of the present disclosure, a process for aromatizing hydrocarbons comprises the process of any of the preceding aspects, further comprising: pre-treating the catalyst under a flow of hydrogen or nitrogen at a temperature from 400° C. to 700° C. for a duration from 1 to 5 hours.

According to a fifteenth aspect of the present disclosure, a process for aromatizing hydrocarbons comprises the process of any of the preceding aspects, wherein the hydrocarbons comprise straight run light naphtha.

According to a sixteenth aspect of the present disclosure, a process for aromatizing hydrocarbons comprises the process of any of the preceding aspects, wherein 100% of the straight run light naphtha undergoes the chemical reaction to form aromatic hydrocarbons.

According to a seventeenth aspect of the present disclosure, a process for aromatizing hydrocarbons comprises the process of any of the preceding aspects, wherein the process yields greater than or equal to 45% by weight of aromatic hydrocarbons.

According to an eighteenth aspect of the present disclosure, a process for aromatizing hydrocarbons comprises the process of any of the preceding aspects, wherein after the contacting, the hydrocarbons comprise aromatics in major proportions and naphthenic hydrocarbons in minor proportions by volume.

According to a nineteenth aspect of the present disclosure, a process for aromatizing hydrocarbons comprises the process of any of the preceding aspects, wherein the contacting the hydrocarbons with the catalyst is performed at a weight hourly space velocity (WHSV) from 1.0 to 20.0 $h^{-1}$, a temperature from 200° C. to 600° C., and a pressure from 1.0 bar to 30.0 bars.

According to a twentieth aspect of the present disclosure, a process for aromatizing hydrocarbons comprises the process of any of the preceding aspects, wherein the aromatic hydrocarbons comprise benzene, toluene, ethylbenzene, xylene, or combinations thereof.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A process for aromatizing hydrocarbons from a hydrocarbon feed comprising:
contacting the hydrocarbons with a catalyst comprising zinc and a metal selected from the lanthanide group dispersed on surfaces of a hydrogen-form medium pore size zeolite support, the zeolite having a silica to alumina molar ratio from 23:1 to 50:1, wherein:
the catalyst is substantially free of gallium and platinum;
the contacting the hydrocarbons with the catalyst is performed at a weight hourly space velocity (WHSV) from 1.0 to 20.0 $h^{-1}$, a temperature from 200° C. to 600° C., and a pressure from 1.0 bar to 30.0 bars; and
contacting the hydrocarbons with the catalyst causes at least a portion of the hydrocarbons to undergo a chemical reaction to form aromatic hydrocarbons;
wherein the hydrocarbon feed comprises from 50% by weight to 99.9% by weight $C_5$ and $C_6$ hydrocarbons based on the total weight of the hydrocarbon feed; and
wherein the process yields greater than or equal to 55% by weight of aromatic hydrocarbons.

2. The process according to claim 1, wherein the hydrogen-form medium pore size zeolite support has a MFI, MEL, MWW, or FER framework type.

3. The process according to claim 2, wherein the hydrogen-form medium pore size zeolite support has a MFI framework type.

4. The process according to claim 3, wherein the hydrogen-form medium pore size zeolite support is a ZSM-5 zeolite.

5. The process according to claim 4, wherein the ZSM-5 zeolite has a silica to alumina molar ratio from 30:1 to 50:1.

6. The process according to claim 4, wherein the ZSM-5 zeolite has a silica to alumina molar ratio from 30:1 to 40:1.

7. The process according to claim 1, wherein the hydrocarbons comprise paraffins, olefins, naphthenes, alkylbenzenes, and combinations thereof.

8. The process according to claim 1, wherein each of the total zinc and metal selected from the lanthanide group present is in an amount of from 0.1 wt. % to 10 wt. %.

9. The process according to claim 1, further comprising:
pre-treating the catalyst under a flow of hydrogen or nitrogen at a temperature from 400° C. to 700° C. for a duration from 1 to 5 hours.

10. The process according to claim 1, wherein the hydrocarbons comprise straight run light naphtha.

11. The process according to claim 10, wherein 100% of the straight run light naphtha undergoes the chemical reaction to form greater than or equal to 45% by weight of aromatic hydrocarbons.

12. The process according to claim 1, wherein the aromatic hydrocarbons comprise benzene, toluene, ethylbenzene, xylene, or combinations thereof.

13. The process according to claim 1, wherein the zeolite has a silica to alumina molar ratio of from 30:1 to 50:1.

* * * * *